United States Patent
Rowlandson et al.

(10) Patent No.: US 7,996,056 B2
(45) Date of Patent: Aug. 9, 2011

(54) METHOD AND APPARATUS FOR ACQUIRING PHYSIOLOGICAL DATA

(75) Inventors: Gordon Ian Rowlandson, Milwaukee, WI (US); David Thomas Peterson, Pewaukee, WI (US); Donald Eugene Brodnick, Cedarburg, WI (US); Robert Edward Henderson, West Bend, WI (US); Chepur Sudhakar Rao, Germantown, WI (US)

(73) Assignee: The General Electric Company, Schenectady, NY (US)

( * ) Notice: Subject to any disclaimer, the term of this patent is extended or adjusted under 35 U.S.C. 154(b) by 1089 days.

(21) Appl. No.: 11/763,952

(22) Filed: Jun. 15, 2007

(65) Prior Publication Data
US 2008/0312520 A1    Dec. 18, 2008

(51) Int. Cl.
*A61B 5/04* (2006.01)
(52) U.S. Cl. ............... 600/386; 600/388; 600/393
(58) Field of Classification Search .......... 600/372, 600/386, 388, 393; 442/117
See application file for complete search history.

(56) References Cited

U.S. PATENT DOCUMENTS

| | | | |
|---|---|---|---|
| 5,546,950 A | 8/1996 | Schoeckert et al. | |
| 6,115,623 A | 9/2000 | McFee | |
| 6,381,482 B1 * | 4/2002 | Jayaraman et al. | 600/388 |
| 6,415,169 B1 | 7/2002 | Kornrumpf et al. | |
| 6,496,705 B1 * | 12/2002 | Ng et al. | 455/502 |
| 6,840,955 B2 | 1/2005 | Ein | |
| 7,171,166 B2 | 1/2007 | Ng et al. | |
| 7,558,622 B2 | 7/2009 | Tran | |
| 2003/0211797 A1 * | 11/2003 | Hill et al. | 442/205 |
| 2005/0054941 A1 | 3/2005 | Ting et al. | |
| 2007/0073131 A1 * | 3/2007 | Ryu et al. | 600/388 |

OTHER PUBLICATIONS

Philips, "Novel Solutions to improve detection of sleep disturbance and early indicators of heart failure," Philips Research Technology Backgrounder, website: http://www.research.philips.com/newscenter/archive/2006/carelab/061025-myheart.html. Date accessed: Feb. 26, 2007.
Office Action dated Nov. 3, 2010.

* cited by examiner

*Primary Examiner* — Lee S Cohen
*Assistant Examiner* — Erin M Cardinal
(74) *Attorney, Agent, or Firm* — Andrus, Sceales, Starke & Sawall, LLP

(57) ABSTRACT

A method and apparatus for the collection of physiological data from a patient is disclosed herein. An electrode assembly comprises an external label identifying an anatomical location and an electrode identifying circuitry that produces a signal indicative of the anatomical location to which the electrode assembly is to be attached. The electrode assembly transmits both the collected physiological signal and the identification signal to a data monitor for collection and processing physiological data.

13 Claims, 6 Drawing Sheets

METHOD AND APPARATUS FOR ACQUIRING PHYSIOLOGICAL DATA

FIELD OF THE DISCLOSURE

The present disclosure relates to the acquisition of physiological data from a patient. More specifically, the present disclosure relates to the reduction of the number of lead wires that must be attached to a patient to obtain physiological data.

BACKGROUND

Electrocardiography (ECG), or the recordation and analysis of the electrical potential of a patient's heart, is one of the most widely used patient physiological monitoring techniques used in healthcare today. In ECG the electrical potentials of various regions of the heart are monitored through the use of electrodes to obtain data that is indicative of the systematic depolarization and repolarization of the heat muscle tissue. Interpretation of this physiological data can be used to identify many cardiac conditions including, but not limited to, bradycardia, tachycardia, ischemia, arrhythmia, myocardial infarction, and drug toxicity. An ECG signal comprises more than the mere collection of biopotentials. Rather, an ECG signal comprises a differential measurement, referred to as a lead, that measures the voltage across the heart between a reference location and a measurement location. Each of the resulting differential leads are denoted by a reference to the physical location of the electrode on the patient used in obtaining that lead.

In a typical 12-lead ECG measurement, ten electrodes are used to obtain the twelve leads. These electrodes include the standard electrode placements at the right arm (RA), left arm (LA), left leg (LL), and right leg (RL). These standard electrodes are supplemented by the addition of six precordial electrodes that are placed at specific locations around the patient's chest and are denoted by the indications V1, V2, V3, V4, V5, and V6.

One major problem with obtaining ECG measurements is that ten separate wires each corresponding to one of the ten electrodes attached to the patient must be used in order to obtain a 12 lead ECG as just described. This can cause a host of problems associated with obtaining ECG measurements. First, the lead wires may restrict physician access to the patient. This limitation on the physician's access to the patient may include the reduced ability of a physician to inspect patient wounds or other anatomical parts due to the large number of lead wires obscuring access. Furthermore, the large number of wire extending from the patient may limit the ability of the physician to attach additional electrodes and lead wires that extend to other patient physiological data monitors, thus impairing the ability to monitor other important physiological parameters of the patient. Furthermore, if a patient requires defibrillation, the electrodes and lead wires must be removed from the patient to prevent damage to the equipment or additional harm to the patient. The more electrodes and lead wires extending from those electrodes, the more difficult it is to quickly and accurately remove all of these connections.

The presently available systems are further undesirable because the large number of lead wires extending from the patient further restricts the patient's movement. The large number of lead wires may restrict where the patient may place his/her arms and/or where and how he/she moves about a hospital bed or room. For example, when a patient is sleeping, the lead wires may restrict the positions in the hospital bed in which the patient may sleep, thus leading to an uncomfortable nights sleep and slower recovery.

Alternatively, due to patient movement or clinician movement about the patient, the lead wires may become tangled. Tangling of the lead wires may lead to electrode and/or lead wire damage. Electrode or lead wire damage results in inaccurate physiological data, resulting in reduced physician ability to diagnose the patient's condition. Furthermore, tangled lead wires may require additional clinician time in removing, untangling, and replacing the tangled electrodes and lead wires with new connections. Additionally, a large number of lead wires may result in the lead wires become tangled while they are in storage and as such, a clinician must spend time before the initial application of the electrodes to untangle the lead wires. The propensity of the lead wires to become tangled also increases the chances of damage to the lead wires. In many instances, if a single lead wire becomes damaged or broken, the entire lead wire set must be replaced at additional cost because the lead wires are individually associated with a specific ECG lead anatomical location.

Attempts have been made to address these and other similar problems, resulting in solutions such as those taught by Schoeckert et al. U.S. Pat. No. 5,546,950 and Kornrumpf et al. U.S. Pat. No. 6,415,169. Solutions such as those presented in the aforementioned patents are summarized with respect to FIG. 1, which depicts an electrode set for obtaining physiological data from a variety of locations on the patient's body.

FIG. 1 depicts an electrode set 10 including a plurality of electrodes 12. Each of the electrodes 12 is connected to an individual lead wire 14. To reduce the tangling of the lead wires 14, all of the lead wires are connected together in the form of an amalgamated lead wire 16. Each of the lead wires 14 extend off of the amalgamated lead wire 16 to provide a limited range of movement within which the clinician can place the electrode 12. The amalgamated lead wire 16 terminates at one end in a plug 18 that comprises a plurality of individual pins (not depicted), each pin associated with one of the lead wires 14 and electrodes 12. When the plug 18 is inserted into a monitoring device (not depicted) the monitoring device associates a specific pin location in the plug 18 with a particular ECG lead to be monitored. To obtain a proper ECG measurement each lead 14 and electrode 12 must be connected to a correct anatomical location on the patient. The proper anatomical placement of the electrode 12 and lead wires 14 may be facilitated by the labeling, or color coding of the lead wires 14 or electrodes 12, such that the clinician may be informed of the proper lead wire 14 and electrode 12 that must be connected to the proper anatomical location. However, due to clinician error, one or more of the lead wires 14 may be connected to an electrode 12 that is located at the improper anatomical position.

Additionally, in the electrode set 10 depicted in FIG. 1, the amalgamated lead wire 16 comprises, or may comprise, a large number of wires. Each additional wire in the amalgamated wire 16 renders the amalgamated lead wires 16 more inflexible, thus decreasing the ability to maneuver the wire, and the patient's overall mobility. Furthermore, in an electrode set 10 comprising an amalgamated lead wire 16 if a single lead wire 14 becomes damaged, the entire amalgamated cable 16 is rendered useless because the ECG lead that the monitoring device associates with the damaged lead wire 14 cannot be measured using that lead set 10. Therefore the entire amalgamated cable 16 must be replaced at added cost.

Therefore, a need exists for an electrode set that limits the number of wires extending from a patient to a data monitor. Furthermore, a need exists for an apparatus and method of using an electrode set that reduces tangling of electrode set lead wires. Additionally it is desirable for an apparatus and method for an electrode set that reduces error in the collection of data due to the connection of a lead wire to an electrode located at an improper anatomical location. Finally, it is desirable for an apparatus and method for an electrode set that may still be used to obtain a full twelve lead ECG measurement despite damage to at least one lead wire.

BRIEF DISCLOSURE

In the present disclosure, an embodiment of an electrode assembly to be used for the collection of physiological data from a patient is herein disclosed. Embodiments of the electrode assembly comprise an electrode that is disposed for contact with the skin of a patient wherein the electrode collects physiological data from the patient. Embodiments of the electrode assembly further comprise a connector connected to the electrode and facilitating the transfer of data from the electrode to a data monitor. Embodiments of the electrode assembly further comprise electrode identifying circuitry that is in communication with the connector. The circuitry may produce a signal that is indicative of the physiological parameter collected by the electrode and transmits this signal to the data monitor to identify the physiological data collected by the electrode.

In a further embodiment of the electrode assembly, the electrode assembly may further comprise a physical identifier in association with the electrode identifying circuitry. Further embodiments of the electrode assembly may comprise an electrode that is a disposable electrode.

An embodiment of an electrode set for collecting physiological data from a patient and transmitting the physiological data to a data monitor is also herein disclosed. Embodiments of the electrode set may comprise a conductor that is disposed to be connected at one end to the data monitor, a connector that is communicatively connected to the conductor and extends away from the conductor, an electrode that is communicatively connected to the connector and is disposed to be attached to the skin of the patient to collect physiological data from the patient. Embodiments of the electrode set may further comprise electrode identifying circuitry between the electrode and the first connector, the electrode identifying circuitry may produce a signal that is transmitted to the data monitor, wherein the signal is indicative of a particular physiological data quantity to be collected by the electrode.

Further embodiments of an electrode set may comprise an external label that is associated with the electrode identifying circuitry wherein the external label corresponds to an identification of physiological data that is transmitted to the data monitor by the electrode identifying circuitry.

Embodiments of the electrode set may further comprise the conductor as a conductive sheet comprising a top side and a bottom side and a first insulating layer in contact with the top side of the conductive sheet and a second insulating layer in contact with the bottom side of the conductive sheet.

A still further embodiment of the electrode set may comprise the connector comprising a female end that extends from the conductive sheet through the second insulating layer and a projection on the electrode that comprises a male end that fits into the female end to make contact with the conductive sheet.

A still further embodiment of the electrode set, the electrode set may be incorporated into a wearable garment.

Additionally a method of obtaining data from an electrode assembly comprising an external label identifying a physiological parameter to be collected by the electrode is herein disclosed. Embodiments of the method may comprise collecting physiological data from the patient at an anatomical location identified by the external label, transmitting the collected physiological data to a data monitor, producing an identification signal that corresponds to the external label on the electrode and to the collected physiological data, and transmitting the identification signal to the data monitor.

DETAILED DISCLOSURE

Figure 1:
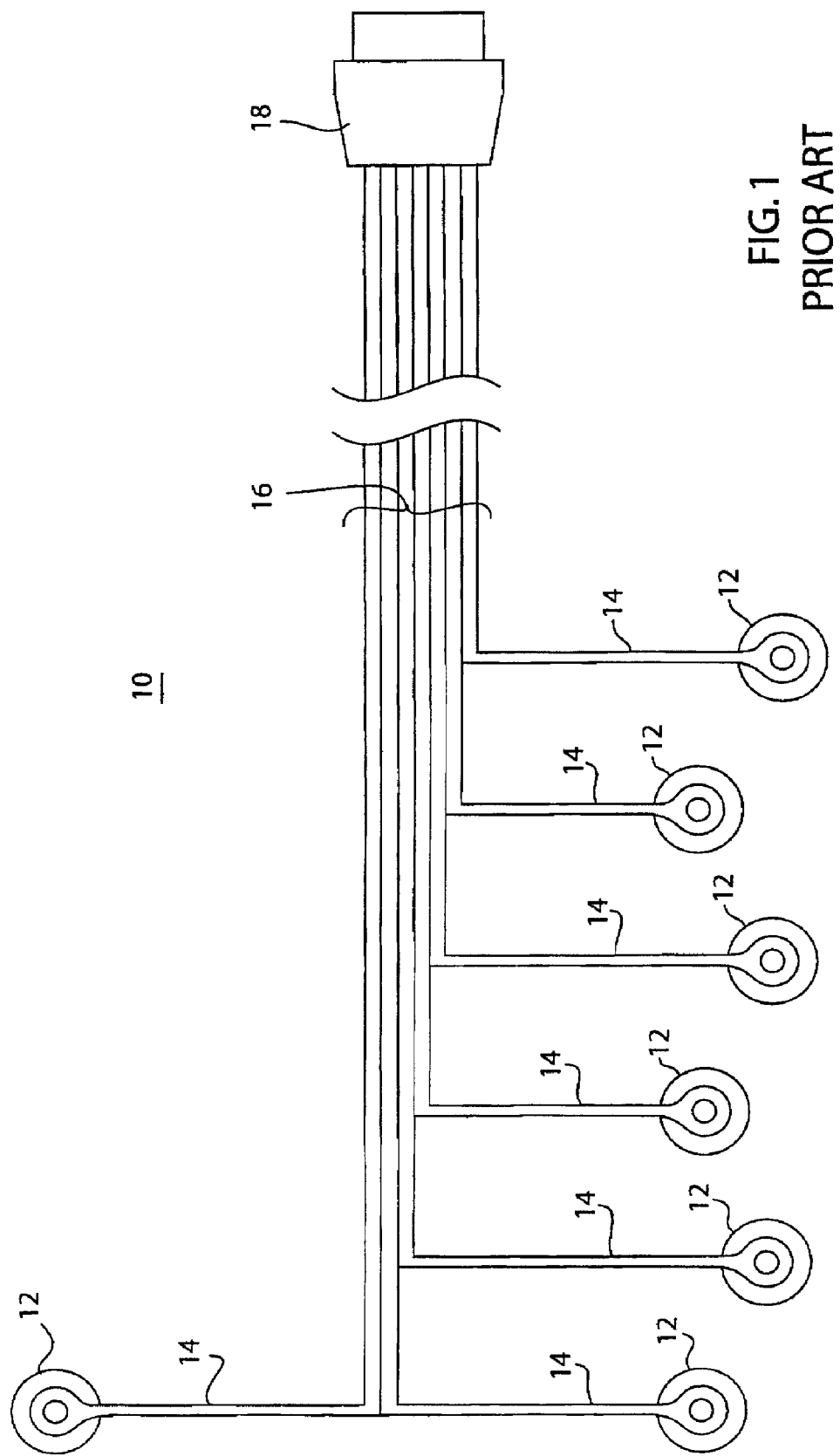
FIG. 1 depicts an electrode set of the prior art.
Figure 2:
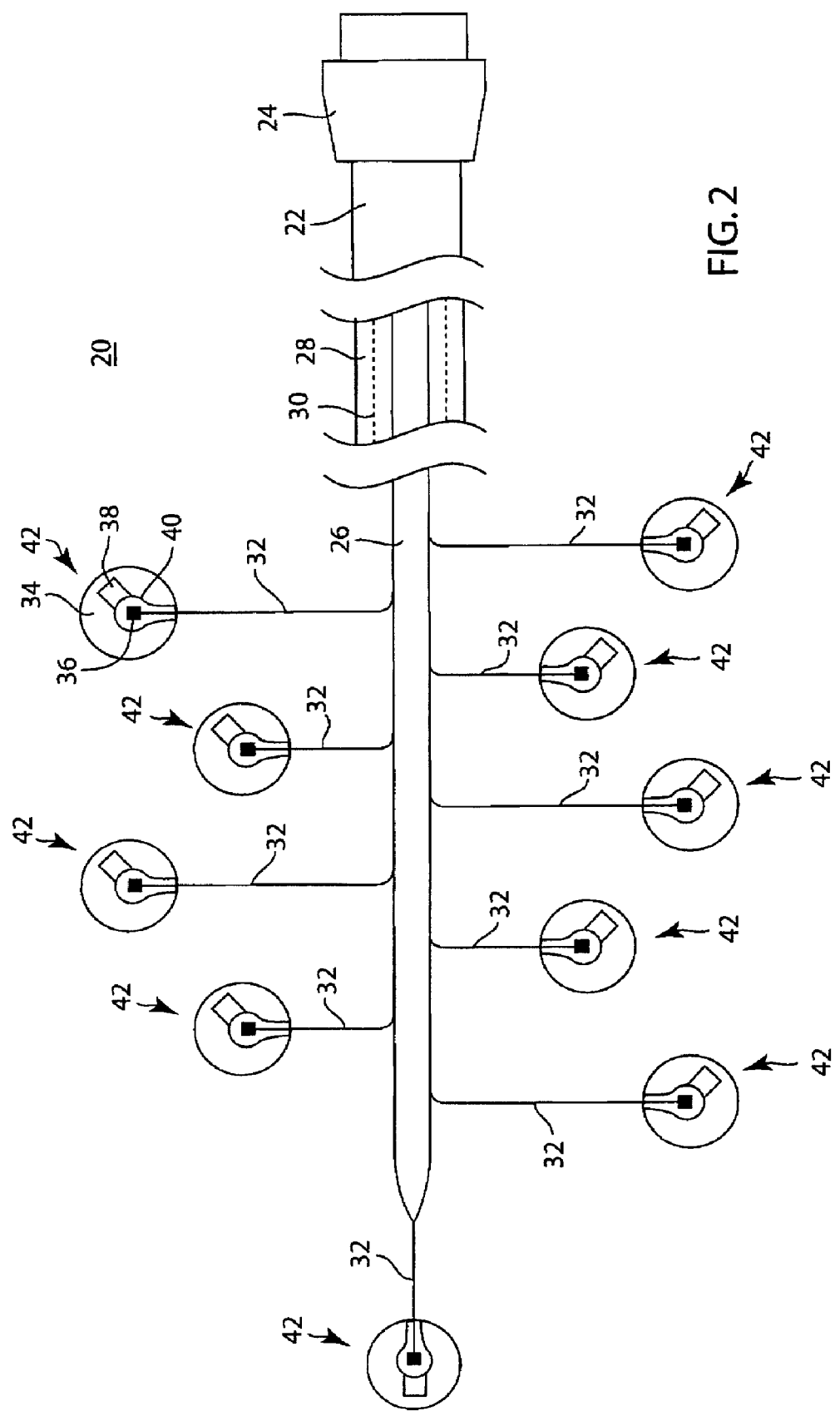
FIG. 2 depicts an embodiment of an electrode set.

FIG. 2 generally depicts an embodiment of an electrode set 20 that is to be used to collect physiological data (i.e. ECG signals) from a patient and transmit the data to a data monitor (not depicted). The electrode set 20 comprises a cable 22 terminating in one end with a plug 24. The plug 24 is disposed to connect to the data monitor for the recordation and processing of the collected physiological data.

The cable 22 comprises a conductor 26 that is coaxially disposed within the cable 22. The conductor 26 is further surrounded by an insulator 28. The insulator 28 serves to insulate the conductor 26 from exposure to electrical charges and to protect people from the electrical charges held in the conductor 26. The cable 22 may further comprise additional shielding 30 that is disposed within the insulator 28 and radially outward from the conductor 26. The shielding 30 provides an additional barrier between any electromagnetic interference from the surrounding area and the conductor 26 that is used to transmit the collected physiological data. At least one connector 32 extends from the conductor 26. More typically, a plurality of connectors 32 extend outward away from the conductor 26. Each of the connectors 32 is communicatively attached to an electrode assembly 42.

As used in the present disclosure, the term connected may refer to a physical and/or a communicative connection. A physical connection involves the physical contact between two elements, while a communicative connection allows the transmission of data between to the two communicatively connected components. A communicative connection may be made between two components through one or more intermediary components.

As illustrated in FIG. 2, the electrode assembly 42 includes an electrode identifying circuitry 36 connected between the electrode 34 and the connector 32 to facilitate the communication of physiological data between the electrode 34 and the connector 32. The electrode identifying circuitry 36 may be surrounded by some type of housing or other protective covering; alternatively, the electrode identifying circuitry 36 may comprise packaging 40 within which the circuitry 36 is disposed. Each electrode assembly 42 may comprise an electrode 34 and electrode identifying circuitry 36.

In an embodiment shown in FIG. 2, an external visible label 38 may be associated with each of the electrode identifying circuitry 36. The external label 38 need not be attached to the circuitry 36 itself, but may be attached to the packaging 40 surrounding the circuitry 36. The label 38 may be a tag that extends from the circuitry 36, or may be another type of indication affixed to the packaging 40. Preferably, the label 38 visually indicates through a symbol, abbreviation, color, or a combination thereof an anatomical location on the patient to which the electrode assembly 42 is to be attached. During the collection of an ECG using the electrode set 20, these anatomical locations may include standard and precordial electrode placements (i.e. LL, LA, RL, V1-V6).

FIGS. 3a-3e depict various embodiments of electrode assemblies 42 that may be used with the disclosed electrode set 20. As depicted in FIGS. 3a-3e, with reference to FIG. 2, the electrode assembly 42 includes the electrode 34, electrode identifying circuitry 36 disposed within a packaging 40, and an external label 38. FIGS. 3a-3e depict various embodiments of the electrode assembly 42 and the connector 32; however, these embodiments are meant to be exemplary of the various electrode assemblies that may be used and is not meant to be limiting on the scope of this disclosure.

Figure 3A:
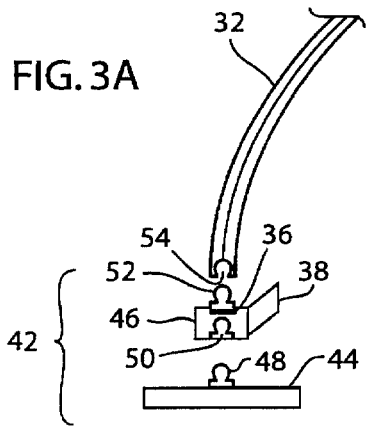
FIGS. 3a-3e depicts embodiments of an electrode assembly.

FIG. 3a depicts an electrode assembly 42 that includes an electrode 44 that is separate from the electrode identifying circuitry 36 located in a package 46 that comprises an external label 38. In this embodiment, the separate electrode 44 may be a reusable type electrode or may be a disposable type electrode. The separate electrode 44 includes a fastener 48 that includes a male ended snap 48 or banana type fastener that connects to a female ended fastener 50 of the packaging 46. A similar male ended fastener 52 of the packaging 46 makes a connection with a female ended fastener 54 of the connector 32.

In using the electrode assembly 42 depicted in FIG. 3a, a clinician may first attach each of the separate electrodes 44 to the desired anatomical locations on the patient, then retrieve the separate packages 46 that comprise the external label 38 and the electrode identifying circuitry 36 and connect each of the packages 46 to the electrode 44 at the anatomical location corresponding to the indication on the external label 38. After all of the electrodes 44 and packages 46 have been connected, the clinician may then connect all of the connectors 32 to the packages 46.

Figure 3B:
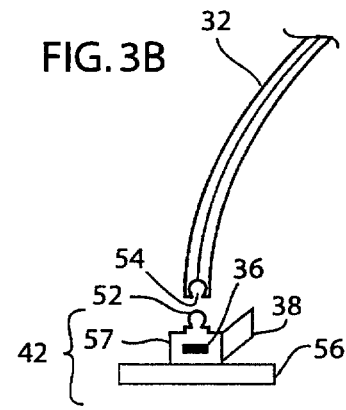

Depicted in FIG. 3b is an embodiment of the electrode assembly 42 that comprises an electrode 56 fixed to a package 57 including the electrode identifying circuitry 36. In this embodiment, the electrode assembly 42 is a single physical component. Due to the added expense of the package 57 and electrode identifying circuitry 36 being attached to the electrode 56, the electrode assembly 42 depicted in FIG. 3b would most likely be used as a reusable type of electrode.

Figure 3C:
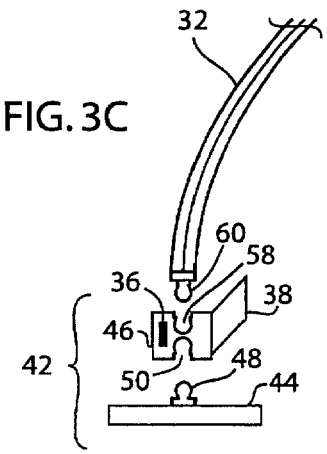
Figure 3D:
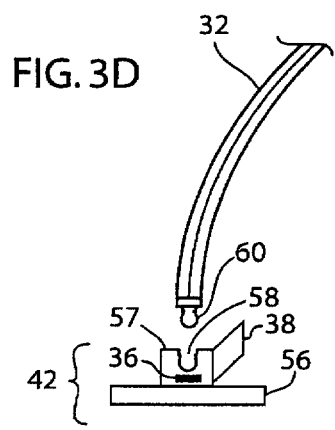

FIGS. 3c and 3d correspond to previous FIGS. 3a and 3b. One of the drawbacks of a conventional electrode 44, whether it is disposable or reusable, is that it is convention to utilize a male-ended fastener 48, 52 on the component that is connected to the patient. This presents safety risks as the male ended fastener 48, 52 may conduct a charge from an outside source to the patient through the electrode 44. In the aforementioned situation, the coupling and conductive properties of the electrode 44 work in reverse, thus projecting more of the rogue charge into the patient. Such a charge, especially when delivered to the chest of the patient may result in macroshock harm to the patient. Therefore, in the embodiments depicted in FIGS. 3c and 3d, the package 46, 57 comprises a female-ended fastener 58 that connects with the male-ended fastener 60 of the connector 32. The embodiment of the electrode assembly 42 depicted in FIG. 3d consists of a reusable electrode assembly 42 including the female ended fastener 58. The electrode assembly 42 depicted in FIG. 3c, however may utilize a separate package 46 with two female ended fasteners 50, 58. The electrode assembly 42 may be used in conjunction with a conventional reusable or disposable electrode 44 and as such, may provide an additional safety feature to already preexisting conventional electrodes 44.

Figure 3E:
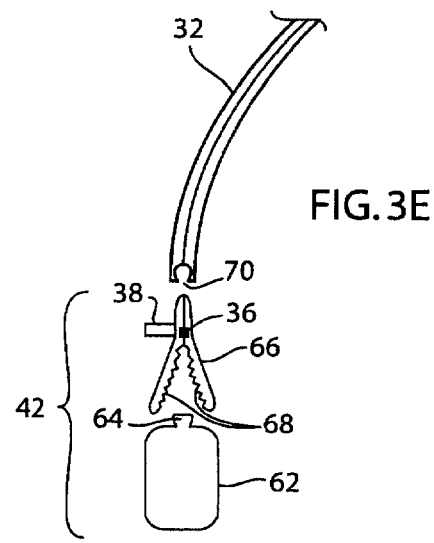

FIG. 3e depicts a still further embodiment of an electrode assembly 42. The electrode assembly 42 depicted in FIG. 3e may be used with disposable tab type electrodes 62. Tab type electrodes 62 are a common form of disposable electrode and do not comprise a male-ended fastener, but rather comprise a tab 64 of a conductive material. The electrode identifying circuitry 36 is held within a specially formed packaging, which is depicted in FIG. 3e as a clip 66. An external label 38 attached to clip 66 designated the anatomical location to which electrode 62 and clip 66 are to be attached. The clip 66 may comprise a pair of alligator jaw fasteners 68 that clip onto the tab 64 of the tab electrode 62. In clinical use, the clinician may first attach the electrode 62 to the patient and then attach the clip 66 to the electrode 62 at the anatomical location as designated by the label 38. Alternatively, the clinician may first attach the clips 66 to the connector 32 via a fastener 70. Then the clinician may attach the clips 66 each of the electrodes 62 at the anatomical location that corresponds to the label 38 on the clip 66.

While the present description is focused on the physical structure of embodiments of the electrode set 20 and 42, much of the functionality of the electrode assembly 42 and electrode sets 20 herein described are derived from the electrode identifying circuitry 36. The electrode identifying circuitry 36 produces a signal that corresponds to the anatomical location specified by the external label 38. Therefore, the data monitor, upon receiving the signal from the electrode identifying circuitry 36, correlates the physiological data obtained by the electrode with the specific anatomical location as identified by the electrode identifying circuitry 36. The external label 38 ensures that the clinician places the packaging with the proper electrode identifying circuitry 36 at the proper anatomical location. As such, the data monitor does not need to correlate or pre-assign any specific lead wire or conductor 26 (FIG. 2) with any one specific anatomical location or physiological data value. Instead, any lead wire 32 of the conductor 26 may be connected to the electrode identifying circuitry 36 and the corresponding electrode 34 (FIG. 2) and the data monitor will receive a signal identifying the location of the electrode such that of the physiological data value collected by the electrode 34 associated with an anatomical location.

The electrode identifying circuitry 36 may achieve this identification function in a wide variety of circuitry implementations. These implementations may be divided into two subsets comprising passive implementations and active implementations based upon the complexity of the operations performed by the electrode identifying circuitry 36. In the passive implementations, the electrode identifying circuitry comprises circuitry that uniquely modifies a characteristic of the returned physiological data signal, or uniquely modifies a carrier signal that is sent to each of the electrodes by the data monitor. The passive implementations may modify characteristics such as, but not limited to, the impedance, frequency or phase of one of these signals. A passive implementation may utilize an RL circuit, RC circuit or another circuit configuration that modifies one of the aforementioned signal characteristics.

Alternatively, active circuitry implementations for the electrode identifying circuitry 36 actively process the collected ECG signal, or a carrier signal injected from the data monitor, to produce a unique indication of the associated anatomical location of the electrode from which the ECG data was collected. Active implementation embodiments of the electrode identifying circuitry 36 may include the use of an RFID tag that wirelessly transmits a signal back to the data monitor that first identifies when that electrode is being sampled, and further identifies the anatomical location to which the electrode is placed. An alternative embodiment of an active implementation of the electrode identifying circuitry 36 is circuitry that uniquely modulates the collected ECG signal or an injected carrier signal either of which are sent back to the data monitor, and the data monitor is able to translate the unique modulation into an identification of the anatomical location of the electrode identifying circuitry 36.

A still further embodiment of an active implementation of the electrode identifying circuitry 36 may comprise an analog-to-digital converter that digitizes the collected ECG signal for transmission back to the data monitor. The digitized signal may then have additional digital identifying data added to the ECG signal as it is transmitted to the data monitor. The data monitor may then interpret the additional identifying digital information, resulting in an identification of the anatomical location where the ECG signal was collected. The examples of active implementations for the electrode identifying circuitry herein previously presented are intended to be merely exemplary of active implementations that may be used in the electrode identifying circuitry and are not intended to be limiting on the scope of the implementations of the electrode identifying circuitry.

The passive implementations and active implementations herein described may result in the transmission of the collected ECG data and the identifying information to the data monitor via a wired data connection. This data connection may comprise the conductor 26, as depicted in FIG. 2. Alternatively, embodiments of the electrode identifying circuitry including active implementations of the circuitry may transmit either or both of the collected ECG data and the identifying data back to the data monitor using wireless transmission of data. This wireless transmission of data may be a wireless transmission of analog or digital data.

Referring back to FIG. 2, the illustrated embodiment of the electrode set 20 comprises a plurality of connectors 32 each connected to one of the electrode assemblies 42 at one end and connected to a conductor 26 at the other end. The conductor 26 is further connected via a plug 24 to a data monitor (not depicted). As previously described, the connectors 32 are detachable from the electrode assemblies 42. In use, a clinician will initially place the electrode assemblies 42 on the proper anatomical locations of a patient, as visually identified by the external labels 38 associated with each of the electrode assemblies 42. Once the electrode assembly 42 has been properly positioned on the patient, one of the connectors 32 is attached to each of the electrode assemblies. Since each of the electrode assemblies 42 include electrode identifying circuitry 36, the selection of which connector 32 to attach to the electrode assembly 42 is irrelevant. As described previously, the electrode identifying circuitry 36 provides a unique signal, either through a passive implementation or an active implementation, such that the monitor device can identify the physical location of the electrode assembly 42 on the patient through the electrode identifying circuitry 36.

The electrode set 20 may comprise a single conductor 26 that facilitates the transfer of the ECG data to the data monitor. To facilitate the transfer of multiple leads of physiological data back to the data monitor via a single conductor, the data monitor must use the conductor 26 as an electrode bus and sequentially sample the signals from each of the electrode assemblies 42. The data monitor may do this in conjunction with the electrode identifying circuitry 36 which may further comprise a gate (not depicted) that allows the ECG signal at the associated electrode 34 to be sampled only upon receiving a signal from the data monitor. The data monitor may send a specific signal that corresponds to opening a gate associated with one of the electrode assemblies 42. The data monitor may then cycle through the individual signals, thus sampling each of the electrodes. If the sampling is done at a fast rate, the time difference due to the sampling can be reduced to a clinically insignificant amount.

The electrode set 20, as depicted in FIG. 2, comprises ten connectors 32 and ten electrode assemblies 42. The electrode set 20 depicted in FIG. 2 would be suitable for the collection of a twelve lead ECG measurement using ten electrodes. In an alternative embodiment, the electrode set 20 may comprise additional connectors 32. These additional connectors 32 may bring the total number of connectors 32 to a number greater than the total number of electrode assemblies 42 to be applied to the patient. The use of the additional connectors 32 gives the clinician additional flexibility when connecting the connectors 32 to the electrode assemblies 42. The connector 32 that is closest and/or most suitable for connection to the electrode assembly 42 may then be the connector 32 that is connected to the electrode assembly 42. As such, the additional connectors 32 may provide the electrode set 20 with the ability to be utilized with patients of a larger variety of body types and sizes. In such a configuration, one standard electrode set 20 may suitably fit a wide variety of patients, including bariatric patients. This advantage is only possible since the connectors 32 are not themselves specifically associated with any anatomical position on the patient, but rather any one of the connectors 32 may be extended to any of the anatomical locations of the patient and the data monitor will still be able to receive an identification of the anatomical location that is the source of a collected ECG signal due to the electrode identifying circuitry 36 of the electrode assembly 42.

In an alternative embodiment of the electrode set, up to four conductors (not depicted) are disposed within the cable 22 that is connected to the data monitor. Each of the four conductors (not depicted) may be additionally connected to each one of the electrode assemblies. The up to four additional conductors may comprise dedicated conductors for different tasks that have herein presently been described to be performed by the single conductor 26. The up to four additional conductors may comprising a reference conductor that transmits a reference signal, which may be the signal from the RA electrode, to each one of the electrode assemblies 42 such that a differential ECG measurement may be obtained from each of the electrode assemblies 42. Another conductor may comprise a communication conductor that transmits the ECG data and/or the electrode identification data back to the data monitor, such that the collected ECG data is not interfered with by any of the other transmitted signals. A still further additional conductor may comprise a power conductor that delivers an AC carrier signal from the data monitor to the electrode identifying circuitry configured in an active implementation, thus providing power to the electrode identifying circuitry. An additional conductor may include an neutral or reference conductor that facilitates the transmission of the ECG data from the electrode assembly 42 back to the data monitor.

As depicted in FIG. 2 the cable 22 may further comprise shielding 30 that is disposed radially outward from the conductor 26. The shielding 30 may comprise a conductor that is referenced to a floating ground in the data monitor. The shielding 30 protects the signals transmitted via the conductor 26 from any outside electromagnetic interference by collecting the interfering signals, pushing the signals out of phase and destructively combining the out of phase interference with the transmitted ECG signal to remove the signal interference. In an electrode set 20, as herein described, this technique of common mode rejection is more effective due to the fact that all of the ECG signals are transmitted via a single conductor and therefore are subject to the same interference signals.

Figure 4:
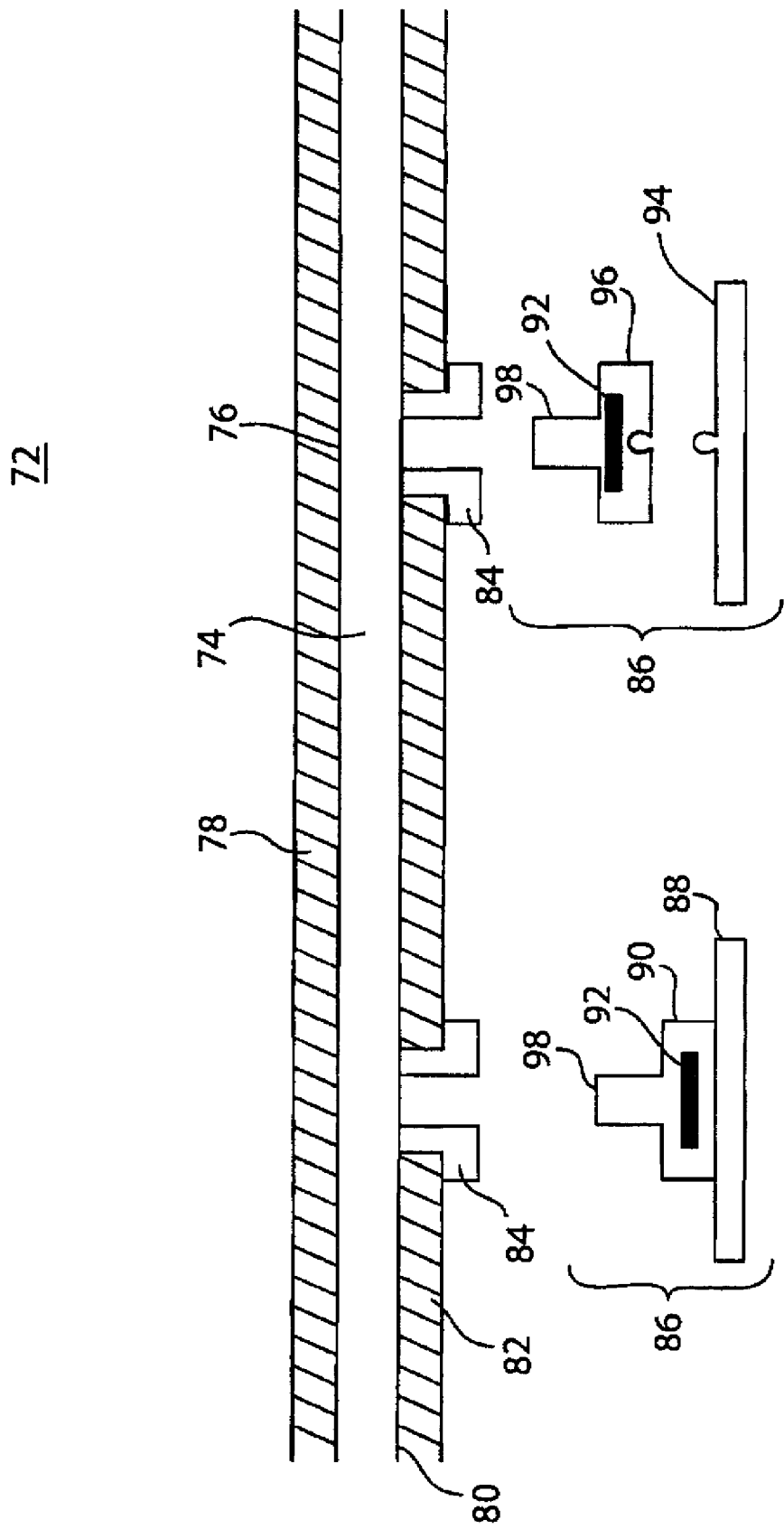
FIG. 4 depicts an alternative embodiment of an electrode set.

Referring now to FIG. 4, an alternative embodiment of the electrode set 72 is herein disclosed. The electrode set 72 comprises a conductor 74; however, the conductor 74 of FIG. 4 differs from the conductor 26 of FIG. 2 in that the conductor 74 is not a wire, but rather takes the form of a conductive sheet 74. The conductive sheet 74 comprises a top side 76 that is insulated by a first insulator 78 that is in contact with the top side 76. The conductive sheet 74 further comprises a bottom side 80. The bottom side 80 of the conductive sheet 74 is insulated by a second insulator 82 that is in contact with the bottom side 80. The electrode set 72 further comprises a plurality of connection buttons 84. The connection buttons 84 extend through the second insulator 82 such that an open path is defined from outside the second insulator 82 to the conductive sheet 74. The electrode set 72 further comprises at least one electrode assembly 86 that includes a unitary electrode 88, packaging 90, and an electrode identifying circuitry 92. Alternatively, the electrode assembly 86 may comprise a detachable electrode 94 and a detachable packaging 96, the packaging 46 including the electrode identifying circuitry 92. Either configuration of the electrode assembly 86 comprises a male fastener 98 that is disposed to be inserted into the open interior of the connection buttons 84. Upon insertion of the male fastener 98 into the connection button 84, the male fastener 98 creates a communicative connection between the electrode assembly 86 and the data monitor (not depicted) via the conductive sheet 74. The male fastener 98 in conjunction with the connection button 84 comprise the functionality of the previously described connector 32 (FIG. 2). As such, the male fastener 98 and connection button 84 are herein considered to be equivalents of the connector 32.

The electrode set 72 operates in a similar functionality as that previously described with respect to the electrode set 20 depicted in FIG. 2, wherein the conductive sheet 74 may be used as an electrode bus wherein samples of the collected ECG signals from each of the electrode assemblies 86 may be transmitted back to the monitoring device.

Figure 5:
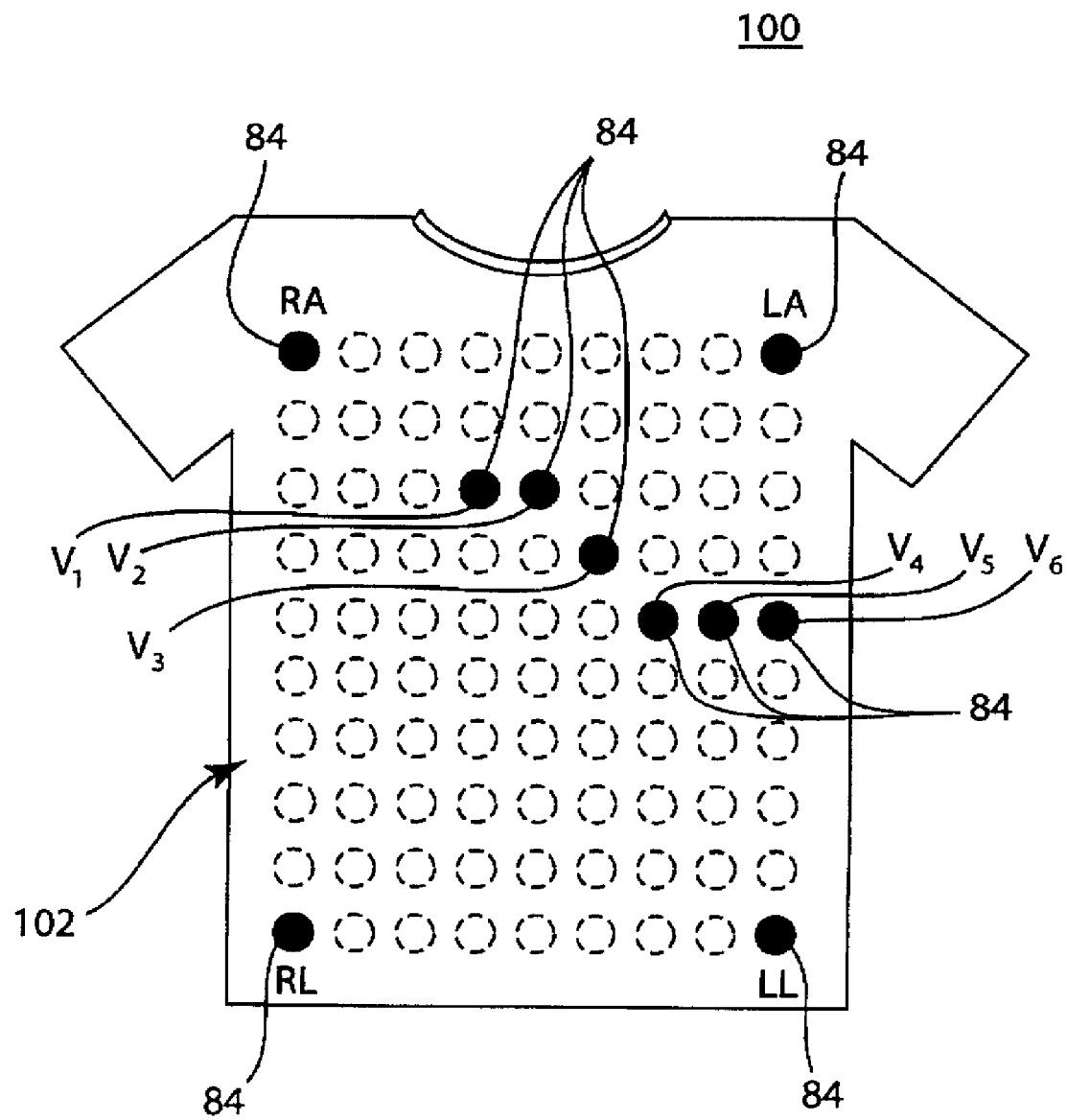
FIG. 5 depicts an embodiment of the electrode set comprising a wearable garment.

The embodiment of the electrode set 72 as depicted in FIG. 4 lends itself to a wide variety of additional applications that may not be realized using conventional electrode set, or the electrode set 20 as depicted in FIG. 2. One such embodiment is a physiological data monitoring garment 100 as depicted in FIG. 5. The garment 100 may be made of a flexible conductive sheet 74 and first and second insulators 78, 82 that are either soft and comfortable, or are covered with a material that is soft and/or comfortable such that the garment 100 may be made incorporating an electrode set 72 (FIG. 4) as depicted in FIG. 5. The electrode set may be laid out in the garment 100 in the form of a grid 102 of connection buttons 84. As previously disclosed, not every connection button 84 must be used to operate the electrode set 102; therefore, the clinician may attach electrode assemblies 86 at only those connection buttons 84 that most closely correspond to the specific anatomical location for which the electrode assembly is designated to obtain a physiological signal.

As depicted in FIG. 5 the darkened in connection buttons 84 disclose a hypothetical arrangement of the electrode assemblies 86 (FIG. 4) as they may be placed by the clinician. A garment 100 such as depicted in FIG. 5 may further reduce any tangling of lead wires experienced in the use of prior art electrode sets by eliminating the lead wires attached to the patient. The patient experiences maximized mobility when wearing the garment and the fear of the tangling or disconnection one of the electrode leads is reduced or eliminated. Therefore an embodiment such as the garment 100 may be a useful embodiment in the monitoring of physiological data of a patient while the patient is sleeping.

Figure 6:
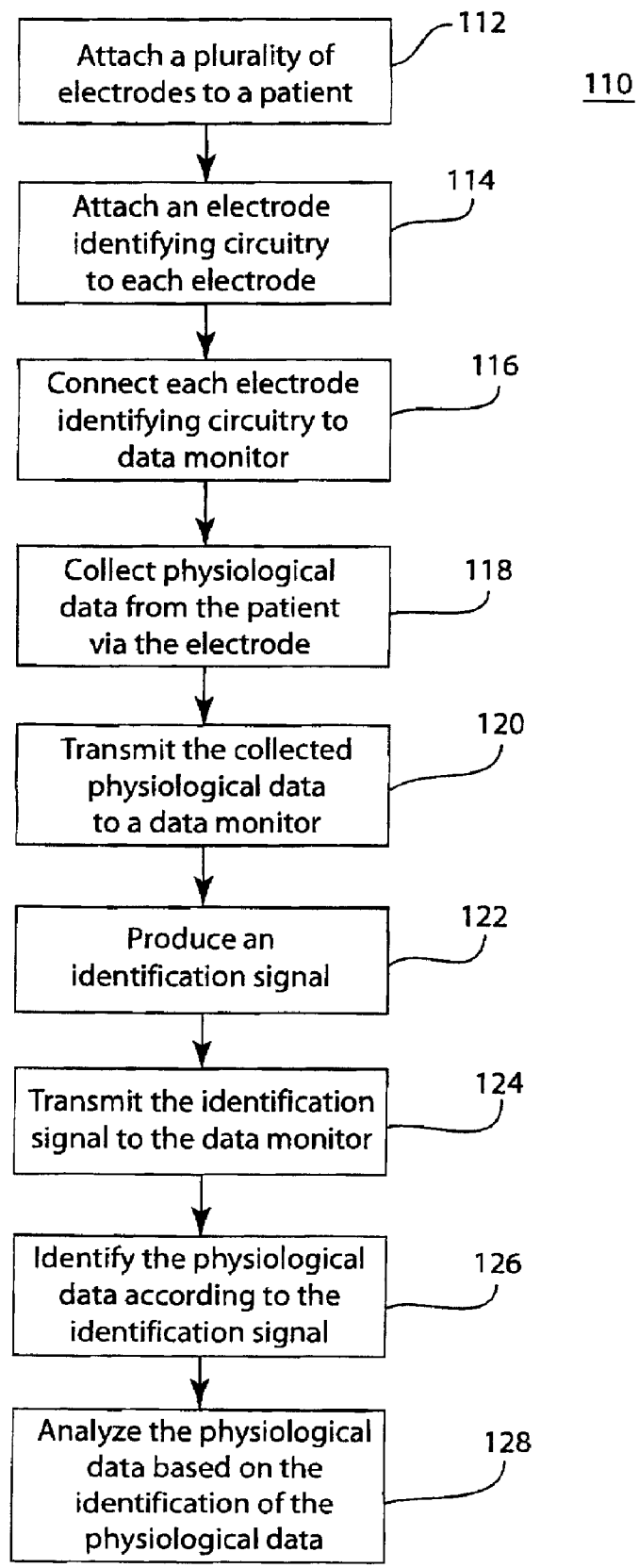
FIG. 6 is a flow chart depicting an embodiment of the method of obtaining physiological data.

FIG. 6 depicts an embodiment of a method 110 for obtaining physiological data from a patient. First, a plurality of electrodes are attached to the patient at step 112. These electrodes may be attached to the patient in no particular order and the electrodes may comprise either reusable or disposable electrodes. Next, electrode identifying circuitry is attached to each of the electrodes in step 114. The electrode identifying circuitry comprises an external label that identifies an anatomic location on the patient to which the electrode identifying circuitry produces an identification of that location. The electrode identifying circuitry must be attached to the electrode at the anatomic location that corresponds with the external label of the electrode identifying circuitry. Above FIG. 6 depicts separate steps 112 and 114 for embodiments that include separate electrodes and electrode identifying circuitry, it is contemplated that in embodiments in which the electrodes and electrode identifying circuitry are incorporated into a single unit, steps 112 and 114 would be combined into a single step in which the integrated electrode and electrode identifying circuitry would be positioned on a patient at locations identified by an identification on the electrode assembly. Such electrode assemblies are illustrated in FIGS. 3b and 3d of the present disclosure.

Next, at step 116 each electrode identifying circuitry is connected to a data monitor through one of the connectors coupled to the conductor for the electrode set. The electrode identifying circuitry may be each connected to the same conductor that is connected to the data monitor or the electrode identifying circuitry may be each connected to separate conductors that connect to the data monitor. Furthermore, there is no need for the electrode identifying circuitry to be connected in any particular order to the data monitor. Next, at step 118 the electrode assembly collects physiological data from the patient via the electrode. The collected physiological data is then transmitted to the data monitor via any intermediary conductors at 120.

Next, at step 122, the electrode identifying circuitry produces an identification signal that corresponds to the anatomical location of the electrode from which the physiological data was collected. The identification signal is transmitted to the data monitor via any intermediary conductors at step 124. The data monitor next identifies the received physiological data according to the identification signal. Finally, the data monitor analyzes the physiological data based on the received identification of the physiological data.

Embodiments of the apparatus and method herein disclosed exhibit advantages over presently available applications and methods. These advantages include the random order placement of electrodes which may be positioned separately from any joining lead wires, cables, or other conductors.

Furthermore, embodiments of the apparatus and method allow the data monitor to automatically identify the electrode position. This provides maximum flexibility in the number of electrodes used in the electrode set as well as the anatomical locations from which data may be obtained using the electrode set. Furthermore, flexibility is achieved as additional physiological data may be sampled at any time by simply editing additional electrode assemblies.

A further advantage achieved by embodiments of the apparatus and method is that the number of conductors within the cable is limited to a minimum. This increases the flexibility and reduces any manufacturing cost associated with the data cables.

A still further advantage achieved by embodiments of the apparatus and method herein disclosed is that the tangling of lead wires is reduced by the reduction and/or elimination of lead wires connected to the patient. The reduction in the tangling of the lead wires also reduces damage to the lead wires and/or disconnection of the lead wires from connection to the patient.

Furthermore, embodiments of the apparatus and method may be alternatively applied to the collection of other physiological signals such as EMG or EEG; however, this is not intended to be limiting on the scope of physiological signals that may be monitored using the apparatus and method herein disclosed.

Another advantage realized by embodiments of the apparatus and method herein disclosed include improved removal of conductive components for providing defibrillation protection to the patient.

Finally, embodiments of the apparatus and method herein disclosed reduce lead placement errors made by clinicians wherein the clinician attaches a lead wire to an electrode at an improper anatomical location on the patient. In embodiments herein disclosed, the electrode assembly identifies the anatomical location of the electrode to the data monitor therefore regardless of the lead wire or conduction connected to the electrode assembly, the data monitor is made aware of the anatomical location from where the ECG signal originated.

This written description uses examples to disclose features of the embodiments, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

What is claimed is:

1. An electrode set for collecting physiological data from a patient and transmitting the physiological data to a data monitor, the electrode set comprising:
    a unitary conductor configured to be connected at one end to the data monitor;
    a plurality of connectors physically connected to the unitary conductor and extending away from the unitary conductor;
    a plurality of electrodes each removably and repeatably communicatively connected to one of the connectors, the electrodes configured to contact the skin of the patient to collect physiological data from the patient; and
    electrode identifying circuitry disposed between the electrodes and the connectors, the electrode identifying circuitry producing a signal indicative of the physiological data collected by the electrode;
    wherein the plurality of physiological data and the plurality of signals indicative of the physiological data are transmitted to the data monitor by the unitary conductor.

2. The electrode set of claim 1 wherein the total number of connectors exceeds the total number of electrodes that may be connected to the connectors.

3. The electrode set of claim 2 wherein each electrode may be independently connected to each of the connectors.

4. The electrode set of claim 1 wherein the electrode identifying circuitry facilitates the control of the transmission of data collected by each electrode to the data monitor via the conductor.

5. The electrode set of claim 4 wherein the circuitry transmits data to the data monitor upon receiving a signal from the data monitor.

6. The electrode set of claim 1 wherein the conductor is a conductive sheet comprising a top side and a bottom side.

7. The electrode set of claim 6 further comprising a first insulating layer in contact with the top side of the conductive sheet and a second insulating layer in contact with the bottom side of the conductive sheet.

8. The electrode set of claim 7 wherein the electrode and circuitry are in communication with the conductive sheet by a projection in communication with the electrode and circuitry projecting through the second insulating layer into contact with the conductive sheet.

9. The electrode set of claim 8 wherein the connector comprises a female end that extends from the conductive sheet through the second insulating layer and the projection comprises a male end that fits into the female end to make contact with the conductive sheet.

10. The electrode set of claim 9 wherein the electrode set is incorporated into a wearable garment.

11. The electrode set of claim 10 wherein the garment is a shirt.

12. An electrode set for collecting physiological data from a patient and transmitting the physiological data to a data monitor, the electrode set comprising:
    a unitary conductor at least partially shielded by an insulative layer, the unitary conductor being communicatively connected to the data monitor;
    a plurality of connectors physically connected to the unitary conductor, each of the plurality of connectors extends away from the unitary conductor through the insulative layer;
    a plurality of disposable electrodes, each electrode of the plurality configured for attachment to the patient, and each electrode acquires physiological data from the patient;
    a plurality of electrode identifying circuitries, each of the electrode identifying circuitries of the plurality being interchangeably connectable to each of the plurality of disposable electrodes and each of the plurality of connectors, wherein each electrode identifying circuitry processes the acquired physiological data to add a signal indicative of an anatomical location to the acquired physiological data.

13. The electrode set of claim 12, wherein the unitary conductor transmits the acquired physiological data from each of the electrodes of the plurality to the data monitor, and the unitary conductor transmits each of the signals indicative of the anatomical location to the data monitor.

* * * * *